United States Patent [19]

Shieh

[11] Patent Number: 5,283,060

[45] Date of Patent: Feb. 1, 1994

[54] BACILLUS-CONTAINING PESTICIDE GRANULES

[76] Inventor: Tsuong R. Shieh, 13100 San Simeon Ave., Bakersfield, Calif. 93309

[21] Appl. No.: 871,425

[22] Filed: Apr. 21, 1992

Related U.S. Application Data

[63] Continuation of Ser. No. 477,006, Feb. 7, 1990, abandoned, which is a continuation of Ser. No. 326,145, Mar. 20, 1989, abandoned, which is a continuation of Ser. No. 193,421, May 12, 1988, abandoned, which is a continuation of Ser. No. 837,435, Mar. 7, 1986, abandoned, which is a continuation of Ser. No. 507,697, Jun. 24, 1983, abandoned, which is a continuation-in-part of Ser. No. 427,604, Sep. 29, 1982, abandoned.

[51] Int. Cl.$^5$ .............................................. A01N 63/00
[52] U.S. Cl. ................................ 424/93 L; 424/93 K; 424/93 M; 424/417; 424/418; 424/420; 514/789
[58] Field of Search ................ 514/789; 424/417, 420, 424/418, 93 K, 93 L, 93 M

[56] References Cited

U.S. PATENT DOCUMENTS

| | | | |
|---|---|---|---|
| 1,738,090 | 12/1929 | Wallace | 424/420 |
| 2,523,420 | 9/1950 | Burrage et al. | 424/420 |
| 3,271,243 | 9/1966 | Cords . | |
| 3,420,933 | 1/1969 | Cords et al. | 424/80 |
| 4,000,258 | 12/1976 | Shieh . | |
| 4,061,488 | 12/1977 | Mann . | |
| 4,094,969 | 6/1978 | Batzer . | |
| 4,166,112 | 8/1979 | Goldberg | 424/93 |
| 4,206,197 | 6/1980 | Goldberg | 424/420 |
| 4,341,759 | 7/1982 | Bogentoft . | |
| 4,376,113 | 3/1983 | Suglia . | |

FOREIGN PATENT DOCUMENTS

| | | |
|---|---|---|
| 263051 | 5/1963 | Australia . |
| 753066 | 1/1971 | Belgium . |
| 2205270 | 5/1974 | France . |
| 1172900 | 12/1969 | United Kingdom . |
| 1557668 | 12/1979 | United Kingdom . |
| 2127690 | 4/1984 | United Kingdom . |

OTHER PUBLICATIONS

Pearman et al. Chem. Abst. vol. 94 (1981) p. 116,034j.
Nitto-Chem. Abst. vol. 94 (1981) p. 116.034j.
Mulla-Down to Earth vol. 23 No. 2 (1967) pp. 15-17.
Banks et al. J. Econ. Entomol. vol. 66 No. 1 241-244 (1973).

Primary Examiner—Sam Rosen
Attorney, Agent, or Firm—Allen E. Norris; Lynn Marcus-Wyner

[57] ABSTRACT

Pesticide granules especially for delivering a biological pesticide in aquatic applications have a wax core and the pesticide secured to the core in a water dispersible or water soluble matrix. More specifically the pesticide composition is free flowing and water floatable with the biological pesticide being of the genus Bacillus and the coating matrix being proteinaceous.

13 Claims, No Drawings

BACILLUS-CONTAINING PESTICIDE GRANULES

This is a continuation of application Ser. No. 07/477,006, filed Feb. 7, 1990, which in turn is a continuation of application Ser. No. 07/326,145, filed Mar. 20, 1989, which in turn is a continuation of application Ser. No. 07/193,421, filed May 12, 1988 which in turn is a continuation of application Ser. No. 06/837,435, filed Mar. 7, 1986, which in turn is a continuation of application of Ser. No. 06/507,597, filed Jun. 24, 1983, which in turn is a continuation-in-part of application Ser. No. 06/427,604, filed Sep. 29, 1982, all of which are now abandoned.

The present invention relates to granular forms of pesticides, e.g. biologicals, their preparation and their use.

Biological substances by nature feed on or attack other substances and hence have been considered for many years as a means of combatting pests, particularly those found in agriculture and the like. For example, bacteria which are thus toxic to insects have been long known and commercial insecticides based on such bacteria have been now available for a number of years. Similarly, viruses are useful against insects while fungi have found use in combatting undesired plants. Biological pesticides have the clear and substantial advantage of being selective or highly specific to particular targets and in general they are environmentally safe. Hence, they have been of increasing interest and attraction in recent years.

Again typical of the biological pesticides, their selective advantage is also one of their drawbacks, restricting markets for the effort expended in development and manufacture. Cost of manufacture and even the availability of different product forms are other significant drawbacks. Most of the drawbacks of the biological pesticide trace to their origin as living natural substances, generally secure in their native environment but otherwise more or less highly sensitive to a wide variety of factors such as heat, light, chemicals and other influences encountered when existing outside of their native environment. Hence, stability, the ability to effectively survive outside of the native environment, is a basic concern and a major prerequisite of the bacterial pesticide. Heat stability, light stability and shelf stability are usually separate problems which must be taken into account and solved. The manufacture of a bacterial pesticide has therefore been largely a matter of achieving the necessary stability while simultaneously providing all of the other properties and characteristics necessary for a commercial product. The result has been, as indicated, higher costs and less flexibility in product forms compared to the synthetic chemicals for similar uses.

For example, *Bacillus thuringiensis*, the more well known commercial bacterial insecticide, became available in wettable powder form, but the separate development of highly specific technology was required in order to obtain an emulsifiable concentrate, see U.S. Pat. No. 3,271,243.

A granular form of a biological insecticide, particularly insecticidal bacteria useful in aquatic applications, has also been of interest but has been generally difficult to develop and typically accompanied by stability and other problems. A prior proposal in U.S. Pat. No. 3,420,933 concentrated on *Bacillus sphaericus*, a bacteria particularly toxic to mosquito larvae, and the use of granules which are at least 20% nonbuoyant in water and prepared from conventional granule core materials such as vermiculite and clays. The recent discovery and availability of *Bacillus thuringiensis* var. Israelensis (hereinafter also "B.t.i."), also particularly potent against insects such as mosquitos and blackflies, has substantially increased the interest in a granular form for a bacterial insecticide, particularly for aquatic applications. Working under this incentive I encountered numerous failures in providing a granular form for a biological until the present invention was made. For examples, it was found that granules prepared with cores of vermiculite, oil coated clay and other conventional or modified materials suffered from a severe loss of potency within about one week from preparation and hence exhibited inadequate storage stability. Most if not all of the test products prepared in a conventional manner were difficult to dispense from conventional granular sprayers or otherwise encountered similar problems. The direction of fall of the lighter granules on aerial application was also difficult to control and unacceptable. In addition, in contrast to the suggestions of U.S. Pat. No. 3,420,933, it has been found that a bacteria for mosquito use is most effective when dispersed and floating at the surface of the water in which the larvae are present. Granules which sink such as those with clay cores were found to be of low effectiveness.

The major objective of the present invention is therefore to provide a new and improved granular form for delivering a pesticide, particularly a biological pesticide.

A further objective of the invention is to provide a stable granular form of a biological insecticide which is capable of floating and releasing its toxicant at the surface of water.

Other objectives will be apparent from the following description of the invention.

In accordance with a preferred embodiment of the present invention, its has been found that a new and improved granular form for a biological pesticide comprises a granular mass in which the individual particles are characterized by having a biological pesticide secured at the surface of a normally solid wax particle core in a system matrix which is non-deleterious to the biological and which is normally sufficiently dry that the particle mass is freely flowable but which matrix is sufficiently water wettable that a pesticidally effective amount of the pesticide is released when the granule is placed in contact with water.

The use of wax as a granule core not only enables the production of a floatable granule but has been found when the invention is followed to provide the basis for a biological pesticide delivery system having potency stability and a number of other desired properties for a granular pesticide particularly useful in aquatic applications. The granules may also be readily produced by a variety of coating procedures followed by such drying as necessary to obtain a free flowing mass.

The invention may be practiced in various forms or embodiments which make the establishment of certain terms and definitions appropriate. In a general sense, the biological pesticide in the final form product is contained within a matrix which in turn is secured to the underlying wax particulate core. Hence, in the simpler embodiments, a more or less uniform or homogeneous matrix material containing the biological pesticide may be directly coated onto the surface of the wax core. In other including certain preferred embodiments the biological pesticide may itself already be encapsulated in a suitably inert material or protecting matrix and the resulting fine particles or powder coated onto and/or absorbed into a first coating of a matrix material already covering the wax core and acting to secure the biological pesticide-containing particles to the core. The matrix securing the biological to the core may be directly or indirectly secured to the core. Thus, indirect securing may be accomplished by first coating or securing to the wax core one or more discreet layers of a suitable inert coating not performing a matrix function and then securing the matrix on the exposed outer surface of the thus coated particle. The precise mechanism by which the biological pesticide is released into water may also vary depending upon the particular embodiment of the invention and type of materials employed. In the simpler embodiments in which the biological is held in a uniform or homogeneous matrix the water must act on the matrix to release the contained biological and this can be accomplished by employing a matrix material which is either water dispersible or water soluble. On the other hand, when encapsulated biological-containing particles are coated onto and/or absorbed into a matrix the result can be a non-homogeous system which in a sense involves a plurality of matrixes within a matrix and the action of water on the different matrixes may be different and the overall release mechanisms may vary accordingly. Thus, the encapsulated biological particles may be, for example, water dispersible or water soluble and the matrix coating in which they are held and secured may be water dispersible, water soluble or water insoluble. For example, the combination of water dispersible encapsulated biological particles on and/or in a substantially water insoluble matrix coating may be employed to lead to the release of the toxicant by wetting of the water dispersible particle portion at the surface of the granule and the resulting drawing of the same into the water. Such action at the surface will generally expose other wettable particles or portions originally within the granule to the wetting and release action such that additional contained amounts of the biological can be drawn in the water and the individual granules having heavy and/or underlying biological content more efficiently utilized. On the other hand, in other and more preferred embodiments, the plurality of encapsulated biological particles are essentially of a water dispersible nature and secured on and/or in an essentially water soluble matrix coating such that the entire matrix system is released from the wax core by the action of water with the individual encapsulated particles essentially dispersing from the site of application. In any case, since different arrangements and wetting susceptibilities such as dispersibility and solubility may be utilized, the terms "water wettable" and the like are used herein to generically designate such water release mechanisms and are applicable to the whole or any portion of the entire biological-containing matrix system secured to the wax granule core as appropriate to release the biological toxicant in the presence of water. It will also be evident that the term "matrix" is used in the broad sense to include systems in which there is a substantially complete embedding in the host matrix and systems in which a substance is only partially embedded and therefore simply held by the host matrix, as well as systems in which a substance is secured by a combination of these two mechanisms. The terms "encapsulated", "encapsulating matrix" and the like are used herein with reference to the biological pesticide to indicate a substantially complete embedding or surrounding of the biologically active substance in the host or matrix material. It will be understood, however, that biologically active pesticides can be encapsulated by procedures basically involving intimately mixing the pesticide with the matrix material, such that a minor portion of the total amount of biologically active substance may be and usually is present or exposed at the matrix surface, even though the pesticide is considered encapsulated as the term is used herein. In addition, whether or not, as in certain preferred embodiments, there are encapsulated or matrixed particles within a matrix, or other essentially non-homogeneous matrix systems, the biological is contained or protected within the granule in the sense of being encapsulated within its more immediate or adjacent matrix. Hence, the term "system matrix" or "matrix system" is generally used without distinction to encompass all or the total of such matrixes which surround and act to secure the biological organism directly and/or indirectly to the wax core, unless distinguished in this text as often will be the case. In one manner of distinguishing, the terms "coating matrix", "matrix coating" and the like will be used to indicate a more or less underlying matrix, distinct in terms of representing an individual coating application or formed from two or more applications of the same coating, which by reason of underlying, embedding, encompassing and/or the like is the sole or principal component of the matrix system in terms of acting to secure a biological directly or indirectly to the wax core, even though as in certain more preferred embodiments the coating matrix by weight may be a small fraction of the system matrix. The coating matrix may be composed of one or more materials,, by no means necessarily mutually soluble or homogeneous, which coating matrix composition is generally uniform but which by definition will not include separately applied or coated materials, e.g., the more or less discreet particles of the biological in an encapsulating matrix when not applied with the coating matrix material or composition. Therefore, as contemplated herein, the system matrix is the essential and total matrix which has an overall encapsulating effect and which will comprise or consist of an equally essential coating matrix.

A wide variety of waxes have a density less than water and may be used in accordance with the invention to prepare pesticidal granules similarly having a density less than water, it being noted that the additional required materials to form the preferred granules of the invention are also lighter than water. If for any reason it might be desired to employ a coating material or additive heavier than water, a wax can usually be selected that will have a sufficiently low density that the resulting granule will nevertheless be buoyant, it being noted that the wax core will generally constitute the majority weight of a practical granule. On the other hand, the wax and resulting granules provided by the invention generally have sufficient weight to penetrate reeds and other similar growth encountered in an aquatic environment and to resist diversion by air currents when applied from the air, all of which are desired capabilities in a granule for mosquito control and the like. The waxes to be used in the invention are normally solid materials in order to retain the integrity of the granules and avoid any undesired fusion of the granules during storage. As a practical matter it is desirable that the wax have a melting point of at least 30° C., and preferably at least 40° C. The preferred waxes have a melting point from 45° C. to 85° C., more preferably 50° C. to 75° C. The wax employed should be inert in the sense of being non-deleterious to the biological pathogen to be incorporated into the granule. A variety of waxes have a chemical composition which is inert to various biological substances and inertness can be routinely ascertained by simple trial and error if necessary. However, in general paraffinic substances are inert to biologicals and the paraffin waxes are preferred as the core material for the granules of the invention. Paraffin waxes having melting points in the more preferred range are readily available commercially in convenient finely divided ("prill") form, for example, Sun Wax 4412 (m.p. 60° C.) and Sun Wax Anticheck (m.p. 67° C.), both from Sun Petroleum Products Company, Wayne, Pa. The wax particulate core may consist essentially of the normally solid wax material or may be body comprising ah inner base surrounded by the normally solid wax material to which the system matrix will be secured, it being only required in such cases that the wax substantially completely coat the base and that such coat be of sufficient thickness such that the base will not adversely affect the insecticide and that water will not penetrate the wax coat such as to cause the total granule to sink at least before its carried pesticide is substantially released on the surface of water. A variety of finely divided or particulate materials may be employed as a base material to be coated by the wax to form the wax particulate core. Such materials themselves desirably have a density less than that of water and may be of a mineral nature such as vermiculite or of an organic nature such as finely divided corn cobs, i.e. the material known as corn cob granules. In any case, any wax core which is a combination of a base material and the wax coating thereon desirably has a density less than water since it is undesirable to depend upon the system matrix and its contained biological to provide a granular product which is buoyant over the desired time to release the biological in water. The amount of base material relative to wax in such wax cores may vary fairly widely and the base material may readily form the greater part of the core on either a weight or volume base. For example, a corn cob granule base material may be employed to form a core containing 75-90% corn cob and 10-25% wax on a weight basis. The principle advantage of employing a base material is a reduction in the cost of the particulate core since a number of readily available base materials are less expensive than waxes. It is accordingly generally preferred that such cores contain from 10% to 60% of wax and from 40% to 90% of base material by weight, more preferably from 15% to 35% by weight of wax and from 65% to 85% of base material, subject to the requirement that the wax substantially coat the base material. Particle size of particulate base material for forming such wax coated base particulate cores is preferably between 0.3 to 3.0 millimeters, more preferably between 1 to 2 millimeters. The resulting wax particulate cores preferably have a particle size between 1 to 4 millimeters, more preferably between 2 to 3.5 millimeters. The cores consisting essentially of the particulate base material surrounded by normally solid wax material may be prepared by conventional procedure for coating a liquified normally solid material on a particulate base. In general, it is preferred to first liquify the wax by heating it well above its melting point, e.g. at least 50° C. above its melting point, preferably 75° C. to 125° C. above its melting point, and then distribute the melted wax onto the mass of particulate base material, e.g. by spraying, accompanied by mixing to insure a thorough and more or less even coating of the wax over the base material. Intense mixing which applies substantial shearing force to the mass is desirable and is continued until the temperature of the wax is well below its melting point, e.g. to virtually room temperature, in order to avoid undesired agglomeration of the resulting individual wax granules or cores. Heating of the mixture either by external means or by the application of an inert heated gas directly into the mass may be employed to insure a thorough distribution of the wax prior to allowing the mass to cool to form the desired cores. When the core consists of wax, the particle size of finely divided wax for use as a starting material in preparing the granules of the invention is preferably between 0.5 to 3.0 millimeters, more preferably between 1 to 2 millimeter.

The system matrix serves two or more functions depending upon the particular embodiment of the invention being employed. In general, the matrix system can adversely affect the stability of the biological and hence is composed of material which is inert in the sense of being non-deleterious to the biological toxicant, while also encapsulating and thus protecting the biological. The coating matrix also serves to secure the biologically active pesticide to the wax core. In addition, when the biologically active substance is substantially completely embedded in the coating or otherwise not releasable into water, the matrix system must also be in whole or in part at least partially water wettable so as to be capable of releasing the active substance as a multiplicity of fine particles of the biologically active substance or of encapsulated active substance.

The particular material to be employed as system matrix material will depend upon the particular biological pesticide to be developed and various factors of choice. Such materials may be carbohydrate in nature, proteinaceous materials from either animal or vegetable sources and selected materials from a synthetic source. The carbohydrates representing the more suitable candidate materials are processed from natural sources and include starches such as corn starch and various cellulosic materials such as ethylcellulose. Proteinaceous materials include by way of example casein, carrageenan, partially hydrolyzed vegetable seed proteins such as soybean protein and partially hydrolyzed animal proteins. Representative synthetic materials include normally solid polyethyleneglycols and polyvinyl alcohol resins. The particular material suitable as a matrix and providing the more inert and stable medium for a particular biological will be usually known for the biologicals which have been investigated and where not known, as in the case of new biological pesticide candidates, can be determined by routine experimentation. However, in general, the proteinaceous materials provide a stable medium for biological pesticide substances such as bacteria, viruses and fungi and may be generally employed.

As indicated, at least the coating matrix of the matrix system also must serve the function of securing the biological to the wax particulate core in addition to providing an inert environment from which the biological is preferably released in water. As will be appreciated, a wax material can be judged inherently to be a poor or unlikely candidate for the core of a granule because its surface offers little or no opportunity for absorption which is the common or principle mechanism by which pesticides are secured in many granular pesticides. Accordingly, particularly in the more practical embodiments in which the coating matrix is secured directly to the wax core, the mechanism of securing is essentially one of surface bonding and generally in the physical sense rather than by chemical reaction. Such physical surface bonding is generally realized by the adhesive properties of materials employed in the coating matrix and such materials are further selected accordingly. The term "adhesive" and the like as used herein will encompass the various properties by which adhesives may effect bonding including such properties and abilities as tackiness, penetration and/or the like, and, in addition, the benefits of cohesiveness as obtained particularly from film forming adhesives. When employing coating matrix material producing water dispersible or other characteristically essentially non-film forming coatings, the property of tackiness becomes a more positive factor in consideration since the oily nature of the wax itself does not provide an ideal bonding surface. Hence, in such non-film forming systems considerations may be also given to maintaining tackiness by allowing an appropriate residual moisture content and storing under conditions which will not rapidly depreciate residual moisture. When less tacky adhesives are employed in the dispersible coating matrixes it therefore may be preferred to avoid storage for as long as the good shelf stability of the product may permit and/or employ granular applicators which do not exert a strong mechanical action on the granules. The use of film-forming coating matrix adhesive materials, such as water soluble hydrolyzed animal protein-a known constituent of envelope glue-therefore is involved in the more preferred embodiments since, inter alia, the contributed cohesive benefit of the resulting film, even though substantially interrupted by contained non-homogeneous particles, is believed to provide overall a particularly effective mechanism for bonding the coating matrix directly, or indirectly, to the wax particulate core.

The system matrix material may be selected from a separate source or even may be present in a biological product as the result of raw materials used in manufacture, or both. For example, bacteria and fungi useful as pesticides are usually produced commercially by fermentation in a nutrient medium comprising water, carbohydrates, proteins and various compatible inorganic salts. The resulting product on a dry basis usually contains a major portion, typically at least 80% by weight, of carbohydrate and protein residues which are at least partially water dispersible and such products may be conveniently used as such as the system matrix material or as a component thereof in preparing the granules of the invention. Fermentation products in which the proteinaceous residue alone is at least 50% by weight of the product on a dry basis are common, and are preferred in the case of fermentation products either for use alone or in admixture with one or more other matrix materials to form a coating composition. Such fermentation batch products may be employed as a coating after making any required adjustments to bring the water content thereof to the desired level, e.g. by evaporation under vacuum. Alternately, the drying of the fermentation batch product, e.g. by spray drying according to known procedures, produces a dry particulate mass in which the particles constitute an encapsulation of the biological pesticide in a matrix composed of the residue of the fermentation nutrient medium. Such particulate mass may be mixed with water to form a tacky, paste-like composition which may be coated onto the wax core to form a granule in which the biological active material is secured in a coating matrix composed of the nutrient residue. On the other hand, and in accordance with the more preferred embodiments of the invention, the dry powder, obtained for example by spray drying of the fermentation batch, is a particularly suitable form to be applied to the wax core particles while still wet from a first coating of matrix coating material. The application of such preferred embodiment to biological pesticides not normally produced by fermentation, e.g. virus pesticides, may also be accomplished. For example, the production of fine particles encapsulating a virus pesticide in a water dispersible proteinaceous matrix has now been described by Rogoff and Shieh, e.g. in British Patent 1,557,668 issued Apr. 8, 1980.

The method of preparing the granules of the invention will vary with the particular embodiment desired to be produced but will be evident from the description of the invention herein. In general, methods of coating liquid compositions onto particles which are uncoated or which have a dried previous coating are known, as are methods of coating dry particles onto particles wetted by a previous coating. When liquid coating is employed, the solvent or dispersing delivery vehicle is desirably water. Organic solvents may be employed but usually must be carefully selected since many can adversely affect the particular biological. In the more preferred embodiments of the invention fine dry particles encapsulating the biological in an encapsulating matrix, for example a so-called technical powder form of a bacterial insecticide such as Bacillus thuringiensis Israelensis, is coated onto and at least partially absorbed into a non-dried matrix coating which has been previously applied to the wax particle. In such a process the wax core material in desired particulate or prill form is agitated or mixed together, e.g. by tumbling in a suitable mixer, and the coating matrix material then sprayed or otherwise applied to the wax particulate mass followed by sufficient continued mixing to coat the coating matrix substantially over the entire surface of the individual wax particles. Such coating is desirably accomplished more or less at room temperature or otherwise below the melting point of the wax. The coating matrix material is suitably applied in the form of an aqueous solution which readily coats the wax and which has sufficient water that the biological pesticide in fine divided encapsulated form can be taken up to a substantial extent in the coating. On the other hand, concentration is sufficiently high that excessive drying desirably can be avoided. Solution concentrations of the order of 20 to 50%, preferably 30–40%, on a weight to volume ratio are suitable in many cases. The amount of coating matrix material on a dry basis may vary depending upon a number of factors including the material employed, thickness of the coating desired, capacity to coat and the like. In general, the amount of coating is very small relative to the weight of the wax core material and may also be relatively minor compared to the amount of the finely divided encapsulated biological pesticide to be later added. For example, the coating matrix in the more preferred embodiments may represent from 0.5 to 5.0% by weight of the wax core material employed, more typically 0.7 to 2.0% by weight of the core. Mixing time to coat the coating matrix solution onto the wax core material will vary but may be accomplished in a relatively short time of from 1 to 20 minutes, more typically 3 to 10 minutes. When such coating is completed, the mixing or other tumbling of the liquid coated wax particulate mass is continued to avoid unnecessary agglomeration and the addition of biological pesticide in finely divided encapsulated form may then be commenced immediately or after a modest delay depending upon the drying characteristics of the matrix coating and the desired amount of pick-up or degree of absorption in the matrix coating. Typically, addition of the biological commences as soon as coating of the coating matrix is complete. The addition of the biological in finely divided encapsulated form is accomplished by controlled and/or intermittent introduction or distribution into the mass of tumbling coated wax particles in order to obtain a more or less even coating of the encapsulated biological particles on the coated wax particles. Addition time may be thus of the order of 1 to 20 minutes, more typically 2 to 10 minutes. The addition of the biological is also preferably conducted at about room temperature and desirably below the melting point of the wax core material As previously indicated, the amount of the matrix material on or in which the encapsulated biological is coated may be relatively minor compared to the amount of encapsulated biological material. For example, the coating matrix material in the more preferred embodiments may represent from 3.0 to 20%, more typically 5.0 to 12% by weight of the encapsulated biological pesticide to be secured to the wax core on and/or in the coating matrix material. Hence, the weight of the encapsulated biological may be from about 5 to 35 times, more typically 8 to 20 times, the dry weight of the coating matrix material. The particular amount of encapsulated biological material to be employed may therefore vary somewhat widely. While controlled at its upper limit by the capacity of the liquid matrix coating solution to take up the encapsulated biological the amount of said encapsulated material may be generally determined by factors of preference and the final desired characteristics of the product such as potency after considering the potency concentration available in the encapsulated biological material being added. On the other hand, the lower limit of the amount of encapsulated material may be influenced by the time necessary to dry the product or otherwise avoid any undesired degree of agglomeration of the particles in the fluid particulate mass. In any event, when addition of the encapsulated biological mass is completed, the resulting particulate mass is maintained in a state of agitation by mixing or tumbling and subjected to drying in order to obtain a product which is a free flowing particle mass. Such drying may be suitably effected with a heated inert gas, such as heated air, which is introduced into the agitated mass. Since biologicals even in protected form are adversely affected by high temperatures, it is usually necessary to control the temperature of the drying conditions or heated gas at modest levels. In general air temperature of from 100° F. to 160° F. may be satisfactorily employed, more suitably air temperatures of from 110° F. to 140° F. It is generally unnecessary to completely dry the mass and a satisfactory product may be obtained on a reduction of the moisture content to at most no more than 10%, preferably to no more than 8% or less. Retention of some moisture may be preferred, as previously indicated. Drying time will vary depending upon particular situations and may range from 15 minutes to 3 hours, but satisfactory drying may be more typically effected in from 25 minutes to 1 hour. On the other hand, drying may be facilitated or essentially carried out at reduced temperatures, e.g. about room temperature, by addition of a moisture absorbing material in substantial quantities, e.g. 50% to 150% of the granular product mass. Such material may then also serve as a diluent for the product. A suitable material for such purpose is (unwaxed) corn cob granule even though such material is unsuitable as a core material when unwaxed. Any agglomerates forming during drying may be broken up, as by hand, and the final product is usually screened according to desired product specifications. Particle size of the product may vary somewhat widely, for example, from 0.5 to 5 millimeters. When employing typical commercially available prill wax forms the particle size of the particles in the final product may vary typically from say 0.5 to 4 millimeters, and in the more preferred embodiments will generally vary from 1 to 2 millimeters. When employing wax coated base cores the final products may vary typically from 1 to 5 millimeters in size, more typically from 2 to 4 millimeters. The resulting product may then be mixed and coated with a small amount, e.g. 0.1 to 4.0% by weight of the granule, preferably 0.5 to 2%, of an anti-caking agent such as calcium stearate, various silicas such as High Sil, Aerosil and the like, as desired.

In the preferred and other embodiments in which fine particles of an encapsulated biological are coated onto wax which is wetted with a matrix coating material the exact nature of the final product will vary depending upon various factors such as the amount of encapsulated material applied to the coating matrix material. The use of only modest amounts of a finely divided encapsulated biological can result more or less in a substantially complete absorption of the biological material into the liquid matrix coating and a more or less substantially complete embedding of the biological containing particles in the finally dried matrix coating. On the other hand, the application of the larger amounts of the biological up to the take up capacity of the liquid matrix coating will result additionally in a significant portion of the biological containing particles being less than fully embedded and only varying portions of some of particles held by the coating matrix and even in some cases tacked as much to each other as to the coating matrix. Under these circumstances the more lightly held biological particles upon complete drying of the product may tend to dust off but this result can be tolerated as well as controlled and is a minor disadvantage compared to all of the advantages offered by the product and the opportunity to deliver a high or maximum dosage with highly loaded particles which will also release the total contained biological at somewhat different times in water. When employing a coating matrix material having film forming properties in the more preferred embodiments described above some or all of the finely divided encapsulated particles containing the biological will penetrate and be absorbed into the liquid matrix coating but the resulting dried coating while non-homogeneous will nevertheless have a lattice, honeycomb and/or other similar effect in which the matrix coating material remains substantially continuously interconnected to provide a cohesive benefit. While not readily subject to description in further detail, these systems, especially employing water soluble matrix coatings, produce a particularly good granule in accordance with the invention. In general, release rates and other characteristics of the final product will also be determined in accordance with the type and amount of material employed as the system matrix or matrix coating, as well as the amount of biological contained therein. Granules prepared in accordance with the invention will release a pesticidally effective amount of the contained biological within a reasonable time of say of up to 24 hours and may be generally prepared in the various embodiments to release at least 80% of the biological within such a time period. However, delayed or very slowed release in a biological granule is not usually considered desirable once in contact with water and the granules of the invention, including particularly those with wettable matrix coatings, are readily capable of releasing at least 50% of the contained biological within 3 hours and 80% within 6 hours.

The present invention may be generally applied to biological substances having use as pesticides, e.g. bacteria, viruses and fungi, all of which classes are represented by various substances already proven in the field and which may be adapted for use in accordance with the invention and its description herein. Bacterial insecticides, particularly of the Bacillus type, are currently more widely investigated and represent a broad class of particular interest. More widely known among the bacteria and Bacillus types are those identified as *Bacillus thuringiensis* (Berliner) although other Bacillus such as *Bacillus sphaericus* will be of immediate interest for use in the invention because of its effectiveness against mosquito larvae requiring aquatic application. See, inter alia, U.S. Pat. No. 3,271,243 and literature cited therein. Current commercial products utilizing *Bacillus thuringiensis* are represented by the varieties Kurstaki and Israelensis. The invention is of most immediate interest for use with said Israelensis (B.t.i.) variety which is currently the clear biological of choice for combatting mosquito, black fly and related larvae pests in an aquatic environment, see U.S. Pat. No. 4,166,112. While the invention has been described with reference to applications in aquatic environments and more specially B.t.i., it will be evident that it may be also readily applied in non-aquatic uses of biological pesticides where granular applications are desired or have been sought, e.g. in reaching insects deep within the folds of crops such as corn.

In addition, the invention has generally demonstrated certain advantages of a wax core for a pesticide granule prepared or readily adapted in accordance with the invention, particularly for but not limited to aquatic applications, e.g. insecticides useful against mosquito larvae, where current granules readily sink and/or exhibit drawbacks overcome by the invention. It is accordingly contemplated that the invention in its broader aspects apply to all substances or agents of a chemical nature useful in combatting pests including synthetic chemicals and non-biological natural substances as well as biological microorganisms. In so applying the invention it will be appreciated that the matrix securing many pesticides to the wax core need not encapsulate the pesticidal substance unless normally required to preserve its stability in one manner or another as a biological needs to be so protected. However, in the practical sense, the invention as described and applied to biologicals herein will preferably be practiced with all chemical agents for combatting pests, e.g. insects, plants, fungi, etc., for examples, by employing matrix coating compositions in which the agent is intimately admixed whereby an essential encapsulation occurs within the final granule in a system matrix secured to the wax core, and particularly by coating conventional wettable powder forms of such agents onto the wax particulate core while wet from a previous coating of a coating matrix coating composition in accordance with all of the general and specific procedures and preferences described herein for the biologicals, whereby a granular product comprising the wettable powder enclosing the agent in a water dispersible matrix is secured to the wax core in a more or less underlying coating matrix which is, as is generally the case with the biologicals, preferably water soluble. It will be evident, however, that a far wide choice of matrix materials and coating vehicles will be available with agents other than biologicals since such other agents usually do not present the stability problems characteristic of biologicals, although the requirement of employing matrix materials and procedures which are non-deleterious to the agent remains.

EXAMPLES AND RELATED INFORMATION

In the following examples Mortality Assays are conducted by filling plastic dish pans measuring $5 \times 11 \times 13$ inches with 8 liters of dechlorinated tap water to provide a depth of 10 cm and surface area of 1 square foot. For each assay 25 larvae of Aedes aegypti (2nd or 4th instar) are added to the pan. Brewer's yeast is also added to each pan at the rate of 25 mg. per liter of water to provide food for the larvae. The assay is then conducted by distributing on the water surface a predetermined amount (rate) of the granules to be investigated and determining the mortality of larvae as a percentage of all larvae originally present at a time from 18 to 24 hours after addition of the granules.

In the examples parts and percentages are by weight unless otherwise stated.

EXAMPLE 1

To a coating mixer is added 95 parts of Sun Wax Antichek prilled paraffin wax (Sun Petroleum Products Company, Wayne, Pa.). The mixer is turned on and there is added to the tumbling mass 20 parts of a paste-like composition prepared by thoroughly mixing 15 parts of water with 5 parts of a technical powder form of B.t.i. that is at least partially wettable and has a potency of 2300 AAU/mg. The B.t.i. powder is prepared in the conventional manner for preparation of a technic B.t. powder by evacuating the contents of the fermentation vat (originally about 6% solids in aqueous medium) to about 14–18% solids of which about 40–60% are proteinaceous and 1–10% starch at a temperature of 40° C. and vacuum of 25–30 in/Hg. and spray drying the resulting mixture. The inlet temperature of the spray dryer is 350° F. and the outlet temperature is 150° F. The mixing after addition of the B.t.i. is continued for about 3 minutes in order to evenly coat the B.t.i. paste onto the wax. While mixing is continued, air heated to about 125° F. is introduced for a period of about 30 minutes and the resulting free flowing granular mass is recovered. The granules are stored for 4 weeks at 40° C. and are then evaluated in the Mortality Assay where the particles float and give a mortality of 100% against the 4th instar larvae 24 hours after application at a rate of 3 pounds per acre.

EXAMPLE 2

A wettable powder of B.t.i. prepare as in Example 1 in an amount of 5 parts is mixed with 10 parts of melted polyethyleneglycol obtained under the designation Polyglycol E400 from the Dow Chemical Company. The mixing is continued from about 2 minutes at a temperature of 40° C. The resulting mixture while still molten is added to an operating coating mixer containing 85 parts of Sun Wax Antichek prilled paraffin wax and mixing is continued for about 3 minutes. The resulting granules are then stored at 40° C. for two weeks and then evaluated in the Mortality Assay where a 100% mortality is observed against the 4th instar 24 hours after application at a rate of 3 pounds per acre.

EXAMPLE 3

To a Stockes tablet coating machine is charged 50 pounds of Sun Wax Antichek prilled paraffin wax. The rotor is turned on and then there is slowly added to the tumbling wax particles 550 ml. of an aqueous colloid protein solution. The colloid protein solution is prepared by mixing 198 g. of a partially hydrolyzed animal protein obtained under the designation Colloid No. 1-V from Swift Adhesives & Coatings with sufficient water heated to a temperature of 60° C. to form a 36% by weight solids solution. The addition of the cooled protein solution takes about 3 minutes and mixing is continued after addition for about 3-5 minutes to evenly cost the protein solution on the wax granules. There is then slowly added onto the tumbling protein coated wax granules 3000 g. of B.t.i. wettable powder prepared as indicated in Example 1. The addition takes place over about 10 minutes and mixing is continued after addition for about 5 minutes to more or less evenly distribute the B.t.i. wettable powder onto the protein coated wax particles. While further continuing the mixing, the resulting particle mass is treated for about 30–45 minutes with dry air heated to a temperature of 50° C. in order to reduce the moisture content to below about 8%. Any lumps in the resulting mass are loosened by hand and the mass then screened to remove any remaining lumps. The resulting product consists of brownish granules with no excess powder formation and is free flowing and the individual particles thereof float on water. The final formation is 87.2 percent wax, 12.0 percent B.t.i. wettable powder and 0.8 percent colloid protein and has a specific gravity of 0.9 quart per pound. Said final granular mass has a potency of 260 AAU/mg. and after 4 weeks storage at 40° C. produces a 100% mortality of the 4th instar 24 hours after application at a rate of 3 pounds per acre in the Mortality Assay. Addition of High Sil silica (1.0% of resulting product) improves the storability of the granules by avoiding agglomeration of the granules.

EXAMPLE 4

To a ribbon blender (Day Model 758) operating at 280 r.p.m. and containing 80 parts (about 100 pounds) of No. 2 corn cob granules (1.5–3 mm) there is added portionwise 20 parts of paraffin wax (same wax as Example 1) which had been preheated to a temperature 150°-170° C. The wax was added in about 4–6 portions from containers whose contents were distributed evenly over the corn cob granule mass. Mixing is continued for about 4 minutes after addition of all of the melted wax during which time the melted wax was more or less evenly coated over the individual corn cob granules and solidified to form a dried wax coating. A charge of 88 parts of the resulting wax coated corn cob granule cores was placed in a similar ribbon blender and mixed together while distributing evenly thereover 4.5 parts the colloid protein solution used in Example 1. Mixing is continued for about 5 minutes after such addition in order to evenly distribute the colloid protein solution over the wax surface of cores. While mixing is continued 10 parts of B.t.i. wettable powder prepared as in Example 1 is evenly distributed over the resulting mass and then mixing is continued for an additional 3–5 minutes to insure an even coating of the powder onto the protein coated wax cores. There is then added 100 parts of No. 2 corn cob granules (unwaxed) and 0.4 part of hydrophobic silica obtained as Aerosil R972 followed by continued mixing for 5 minutes to obtain a uniform mixture. The addition of the unwaxed corn cob granules facilitates drying of the mass and serves as a diluent in the product. The resulting mass is screened through a No. 6 mesh screen (0.132 inch) to obtain the final granular product. These granules produce a 100% Mortality of the 4th instar after 24 hours in the Mortality Assay when applied at a rate of 2 pounds per acre and after storage for 3 weeks at 40° C. provide mortalities against the 4th instar in the Mortality Assay of 85% and 100% when applied at the 2 pound and 4 pound per acre rates respectively. When applied to water by overhead freefall application about 98% of the granules remain afloat on the water surface 24 hours after application. Granular spray and foliage penetration characteristics of the granules are judged to be excellent, as are the freefall characteristics of the granules.

It will be evident that the products of the foregoing examples and others prepared in accord with the invention to contain a mosquito larvicide provide a particularly useful and improved granule for combatting mosquito larvae in an aquatic environment containing the same by overhead application, i.e. above the water and any vegetation, e.g. reeds, growing therein.

While certain preferred embodiments have been described and emphasized in detail, it will be evident that various other embodiments and modifications within the scope of the invention and its disclosure hereinabove will occur to those skilled in the art.

What is claimed is:

1. A free flowing and water floatable granular form of a biological pesticide from the genus Bacillus comprising a particle mass in which the individual particles comprise; a) a particulate core having a surface of normally solid paraffin wax, said core consisting essentially of normally solid paraffin wax or finely divided or particulate material coated with a normally solid paraffin wax; b) a coating matrix of a water-soluble proteinaceous adhesive material secured to said paraffin wax surface; and c) a biological pesticide from the genus Bacillus, encapsulated in a water dispersible matrix secured in said water-soluble proteinaceous coating matrix, said particulate core having a density which is less than the density of water and said particle releasing a pesticidally effective amount of said pesticide when placed in contact with water.

2. A granular pesticide according to claim 1 in which the particulate core comprises finely divided or particulate material coated with a wax.

3. A granular pesticide according to claim 2 in which the finely divided or particulate material is corn cob granule.

4. A granular pesticide according to claim 1 in which the particulate core consists essentially of wax.

5. A granular pesticide according to claim 3 in which the paraffin wax has a melting point of at least 40° C.

6. A granular pesticide according to claim 1 in which the Bacillus is *Bacillus thuringiensis* var. Israelensis.

7. A granular pesticide according to claim 5 in which the Bacillus is *Bacillus thuringiensis* var. Israelensis.

8. A granular pesticide according to claim 7 in which the proteinaceous adhesive material is a film-forming, adhesive material.

9. A granular pesticide according to claim 8, in which the film-forming adhesive material is hydrolyzed animal protein.

10. A granular pesticide according to claim 9 in which the coating matrix by weight is from 0.5 to 5% of the wax particulate core and the coating matrix by weight is from 3 to 20% of the combined weight of the water dispersible matrix and biological encapsulated therein.

11. A granular pesticide according to claim 9 in which the water dispersible matrix encapsulating said biological pesticide from the genus Bacillus is composed of a fermentation residue comprising carbohydrate and at least 50% by weight of proteinaceous residue.

12. A method of combatting mosquito larvae in an aquatic environment comprising distributing into said environment by overhead application a mosquito larvicide effective amount of a granular pesticide of claim 5.

13. The process of producing a water-floatable granular form of a biological pesticide from the genus Bacillus comprising coating a plurality of normally solid paraffin wax core particles with an aqueous matrix coating composition comprising a water-soluble proteinaceous adhesive matrix mixing the thus coated wax particles while still wet with fine divided particles constituting an encapsulation of a biological pesticide from the genus Bacillus in a water dispersible matrix and drying the resulting mass to remove sufficient moisture to obtain a free flowing particulate mass, said paraffin wax core having a density less than water and said paraffin wax core, coating matrix and encapsulating matrix being inert with respect to the biological pesticide from the genus Bacillus.

* * * * *